US00PP11740P2

(12) United States Plant Patent
Boeder

(10) Patent No.: US PP11,740 P2
(45) Date of Patent: Jan. 16, 2001

(54) CHRYSANTHEMUM PLANT NAMED 'CLEAGAR TNG1'

(75) Inventor: Mark Boeder, West Wittering (GB)

(73) Assignee: Cleangro LTD (GB)

( * ) Notice: Under 35 U.S.C. 154(b), the term of this patent shall be extended for 0 days.

(21) Appl. No.: 09/189,712

(22) Filed: Nov. 11, 1998

(51) Int. Cl.[7] ..... A01H 5/00
(52) U.S. Cl. ..... Plt./297
(58) Field of Search ..... Plt./286, 297

(56) References Cited

U.S. PATENT DOCUMENTS

P.P. 1,129 * 9/1952 Boerner ..... Plt./293

OTHER PUBLICATIONS

UPOV–ROM, 1999/02, Plant Variety Database, GTI Jouve Retrieval Software, citation for 'Tanager'.*

* cited by examiner

*Primary Examiner*—Howard J. Locker
(74) *Attorney, Agent, or Firm*—Mark K. Dickson; Howrey Simon Arnold & White, LLP

(57) ABSTRACT

A new plant variety of chrysanthemum producing pale pink daisy-type flowers and darker pink buds.

1 Drawing Sheet

BACKGROUND OF THE INVENTION

The present invention is directed to a new and distinct variety of chrysanthemum (*Dendranthem grandiflora*). The varietal denomination of the new chrysanthemum is 'Cleagar TNG1'.

The female parent of the new variety is the variety known as 'Vera' and the male parent is a undistributed seedling identified as 'G63-C76'. The new variety has been asexually reproduced by vegetative cuttings in Ventura County, Calif. and the distinguishing characteristics are retained through successive generations of asexual reproduction.

SUMMARY OF THE INVENTION

'Cleagar TNG1' is a chrysanthemum plant variety producing pale pink daisy-type flowers and darker pink buds.

BRIEF DESCRIPTION OF ILLUSTRATIONS

The accompanying photograph shows typical specimens of the plant and flowers of the new variety with colors being as nearly true as possible with illustrations of this type.

DESCRIPTION OF THE PLANT

The following description of the new variety is of specimens grown in a greenhouse in Ventura County, Calif. in the month of April. 'Cleagar TNG1' has not been observed under all possible environmental conditions. The phenotype may vary with variations in the environment such as temperature, light intensity, day length and cultural conditions. The color designations herein are from The Royal Horticultural Society Colour Chart except where general terms are used.

To produce a commercial product the plants may be pinched once about ten days after planting. It has been observed that the shelf life of 'Cleagar TNG1' is about 24 days and response time is about 6.5 weeks. No treatment with growth retardant was used with plants described. Useful growing conditions include night temperatures of about 62°–65° F., day temperatures of about 70°–75° F. The new variety is naturally blooming in early September in Ventura County, Calif., but is obviously dependent upon climate conditions in any particular year, and condition of the plant.

Plant:
- *Habit.*—Mounding herbaceous perennial.
- *Height.*—About 26 cm.
- *Number of breaks from pinch.*—About 4.
- *Length of lateral branches.*—About 21 cm.
- *Stem color.*—Near 146D.

Foliage:
- *Leaf arrangement.*—Alternate.
- *Number of leaves per lateral branch.*—About 14 fully expanded leaves.
- *Leaf size.*—Length: About 6.1 cm. Width: About 3.5 cm.
- *Leaf shape.*—Ovate.
- *Attachment.*—Petioled.
- *Leaf apex.*—Acute.
- *Base.*—Truncate.
- *Margin.*—Palmately lobed, serrate.
- *Aspect.*—Slightly undulate.
- *Surface.*—Top: Lightly pubescent. Bottom: Lightly pubescent.
- *Venation Color.*—Upper side: Near 144B. Underside: Near 137D.
- *Petiole.*—Length: About 1.6 cm. Color: Near 144A.

Color:
- *Mature leaf.*—Top: Near 137A. Bottom: Near 137B.
- *Young leaf.*—Top: Near 137C. Bottom: Near 138B.

Bloom:
- *Inflorescence form.*—Cyme.
- *Flower form.*—Daisy.
- *Number of blooms per branch.*—About 8.
- *Diameter of fully expanded bloom.*—About 4.5 cm.
- *Diameter of disc.*—About 1 cm.

*Depth of fully expanded bloom.*—About 1.5 cm.

*Sepal number.*—About 25. Color: Near 137B.

*Peduncle.*—Length: Peduncle length is shortest at the terminal flower and progressively longer moving down the stem; the longest peduncle length is on average 6.5 cm, the shortest peduncle length is on average about 2.8 cm. Habit: Slightly curved. Surface: Pubescent. Color: Near 144A.

*Flower bud* (*when just showing color*).—Color: Near 54C. Diameter: About 1 cm. Height: About 0.8 cm.

*Ray florets.*—Number per flower: About 45. Texture: Matte. Shape: Oblong. Apex: Obtuse. Base: Truncate. Margin: Entire. Aspect: Slightly undulating. Length: About 2.2 cm. Width: About 0.5 cm.

*Disc florets.*—Number per flower: About 90. Texture: Shiny. Shape: Cylindric. Margin: Entire. Length: About 0.5 cm. Width: About 0.1 cm.

Frangrance: Strong, musky.

Flower color:

*General flower coloration.*—Soft pink daisy-type with a yellow eye.

*Ray florets, top side.*—Immature: Near 62C. Mature: Near 62D. Fading: Near 56D.

*Ray floret, under side.*—Immature: Near 62B. Mature: Near 62C. Fading: Near 62D.

*Disc florets.*—Immature: Near 154B. Mature: Near 12A. Fading: Near 14B.

Changes as the flower ages: Disc color darkens, ray florets fade in color and become more undulating.

Reproductive organs:

*Ray florets.*—Pistillate. Stigma shape: 2 branched. Stigma color: Near 12A. Style length: About 0.4 cm. Style color: Near 2D.

*Disc florets.*—Stigma shape: 2 branched. Stigma color: Near 13A. Style length: About 0.3 cm. Style color: Near 1D. Stamen number: About 5. Anther length: About 0.2 cm. Pollen color: Near 15A. Pollen quantity: Abundant.

What is claimed is:

1. A new and distinct chrysanthemum plant of the variety substantially as herein shown and described.

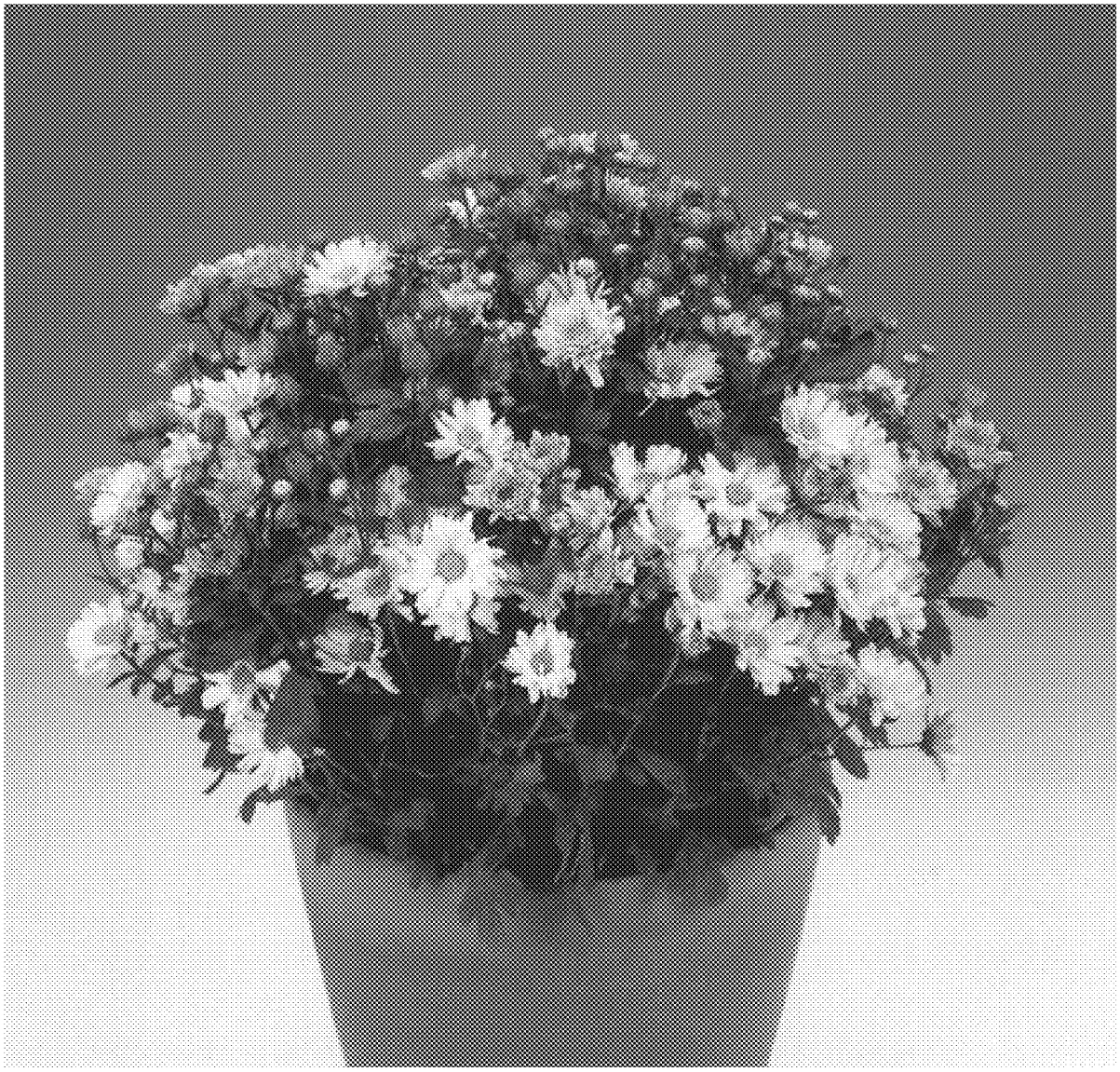

* * * * *